United States Patent
Zanotti-Russo

Patent Number: 6,140,435
Date of Patent: Oct. 31, 2000

[54] CROSS-LINKED ACRYLIC COPOLYMERS IN AQUEOUS EMULSION WITH IMPROVED THICKENING AND SUSPENDING PROPERTIES

[75] Inventor: Matteo Zanotti-Russo, Bergamo, Italy

[73] Assignee: 3V, Inc., Weehawken, N.J.

[21] Appl. No.: 09/056,871

[22] Filed: Apr. 8, 1998

[30] Foreign Application Priority Data

Apr. 9, 1997 [IT] Italy .................................. MI97A0811

[51] Int. Cl.$^7$ ........................ C08F 222/10; C08F 267/00
[52] U.S. Cl. .................................. 526/238.2; 526/318.41; 526/318.44; 526/321; 526/932; 524/916; 525/384; 525/385; 525/386
[58] Field of Search .......................... 526/238.2, 318.41, 526/318.44, 321, 932; 524/916; 525/384, 385, 386

[56] References Cited

U.S. PATENT DOCUMENTS 4,138,381  2/1979  Chang et al. .
4,769,167  9/1988  Haas et al. ............................... 526/932
4,800,220  1/1989  Ribba .

FOREIGN PATENT DOCUMENTS 0 013 836  8/1980  European Pat. Off. .

*Primary Examiner*—Tae Yoon
*Attorney, Agent, or Firm*—Birch, Stewart, Kolasch & Birch, LLP

[57] ABSTRACT

Cross-linked copolymers possessing high thickening and suspending properties obtainable by polymerization of monomeric systems comprising a) 10–97% of at least one unsaturated carboxylic acid, b) 0–80% of at least one alkyl ester of an unsaturated acid, c) 0.5–80% of an associative monomer, d) 0–20% of an unsaturated amide, e) 0.2–20% of a suitable cross-linking agent and f) 0–20% of an unsaturated sulfonic acid; processes for their preparation, which comprise polymerization by precipitation, suspension and solution polymerizations or emulsion polymerization; latexes comprising up to 50% or more of said copolymers; said cross-linked copolymers and said latexes whenever prepared by the above polymerization processes; their use as thickening agents of aqueous, or substantially aqueous systems; and the new cross-linking agents.

20 Claims, No Drawings

CROSS-LINKED ACRYLIC COPOLYMERS IN AQUEOUS EMULSION WITH IMPROVED THICKENING AND SUSPENDING PROPERTIES

The present invention refers to cross-linked copolymers possessing high thickening and suspending properties, their use in aqueous systems and the processes through which these copolymers can be obtained.

BACKGROUND OF THE INVENTION

In the literature, including the patent literature, various thickening agents derived from poly(meth)acrylic acid, optionally copolymerized with cross-linkers, are described. As an example, U.S. Pat. No. 2,798,053 reports thickeners known as CARBOPOL®, obtained as powders by precipitation of the copolymer from different solvent systems and subsequent drying. However, the handling of volatile powders makes their use problematic and limits their corresponding employment; in addition, the aqueous dispersion of said products reaches high vicosities even at low concentrations, thus hampering their use in the form of stable suspensions.

In British Patent 870,994, the preparation of copolymers of methacrylic acid with alkyl acrylates is described, in which said copolymers are synthetized in concentrated (25–50% of solid content) and fluid aqueous emulsions.

In U.S. Pat. No. 4,138,381, the unsaturated carboxylic acids are copolymerized with alkyl acrylates and with esters between (meth)acrylic acid and polyethoxylated (5–80 moles of ethylene oxide) fatty alcohols ($CO_{0-20}$), for the purpose of obtaining a better thickening power and a reduced sensitivity towards the salts present in the solution to be thickened. The polymerization described in this patent is carried out in glycol or in a 50% water-glycol mixture.

EP A1 0013836 reports the copolymerization in aqueous emulsion of (meth)acrylic acid with alkyl acrylates and an ester of (meth)acrylic acid with a ($C_{8-30}$) alkyl, alkylaryl or polycyclic alkyl monoether of a polyethyleneglycol. The polymerization is optionally carried out in the presence of a cross-linking agent, which, however, is employed in quantities never higher than 1%, calculated on the total weight of the monomers. Products are obtained endowed with thickening properties which, in addition, possess an acceptable resistance towards the electrolytes which may be present in the variuos systems to be thickened.

Similarly, in EP A1 0109820 and EP B1 0217485, cross-linked copolymers are described, which are prepared by polymerization in aqueous emulsion and in which the cross-linking agent, when employed, is again present in quantities which are never higher than 1%, calculated on the total weight of the monomers. Also these copolymers seem to possess a reduced sensitivity towards electrolytes.

EP A1 0658579 reports the preparation of non cross-linked thickening agents deriving from the copolymerization of a monomeric system consisting of, among others, (meth) acrylic acid, an ester of (meth)acrylic acid and an associative monomer which is the sorbate of an O-alkyl-polyoxyethylene glycol.

Finally, in WO 96/35757, aqueous print pastes are described which are thickened by cross-linked copolymers having a particle size higher than 200 nm. These copolymers are obtained by polymerization in aqueous emulsion of a (meth)acrylic acid/(meth)acrylate/allyl-O-PEG-O-alkyl system in the presence of a cross-linking agent which is preferably employed in amounts not higher than 0.05%; it is also represented that, in order to obtain an aqueous print paste possessing improved color yield, the polymerization is advantageously carried out in the presence of ethoxylated alcohol phosphates as surfactants/emulsifiers.

DETAILED DISCLOSURE OF THE INVENTION

The present invention refers to new cross-linked copolymers showing high thickening and suspending properties, their use in aqueous, or substantially aqueous systems, and the processes by which these copolymers can be obtained.

For example, these processes can be precipitation polymerizations, suspension and solution polymerizations, or emulsion polymerizations of the type oil-in-water or water-in-oil. Preferred is the oil-in-water emulsion polymerization process, through which latexes of the cross-linked copolymers of the invention can be obtained with a solid content up to 50% or more. These latexes, which form a further object of the invention, are easy to be handled (if compared, for example, with the CARBOPOL®s, which are powders), remain fluid up to a pH of about 6, and can be employed as such or diluted to a predetermined degree depending on the envisaged use. Thus, when these latexes, or the corresponding diluted emulsions, are added to an aqueous, or substantially aqueous system and, in turn, this is added with an organic or inorganic base, or with a mixture thereof, so as to bring the pH of the system to a pH value higher than about 6, a marked increase of the viscosity of the same system is observed. This feature makes these copolymers useful as thickening and suspending agents for a wide variety of uses, as an example, in the cosmetic and textile industry. In fact, it has surprisingly been found that the copolymers of the present invention possess higher suspending properties in comparison with the art-known copolymers of (meth)acrylic acid, that also the thickening properties of the emulsions according to the invention are higher if compared with those of the art-known polymeric emulsions, and that their thickening properties are not substantially influenced by the presence of electrolytes. Furthermore, the viscosity and the rheology of the aqueous, or substantially aqueous systems thickened with the cross-linked copolymers of the invention remain substantially unaltered for a long time.

Accordingly, an object of the present invention is represented by cross-linked copolymers obtainable by copolymerization of a monomeric system comprising:

a) from about 10 to about 97% by weight of at least one ethylenically unsaturated mono- or dicarboxylic acid;

b) from 0 to about 80% by weight of at least one ($C_{1-20}$) alkyl or aralkyl ester of an ethylenically unsaturated mono- or dicarboxylic acid;

c) from about 0.5 to about 80% by weight of at least one associative monomer which is an ester of formula

$$A\text{—}O\text{—}(CH_2\text{—}CHR_2O)_x\text{—}(CH_2)_y\text{—}R_1$$

wherein

A is an ethylenically unsaturated acylic residue, optionally containing an additional carboxylic group, wherein, optionally, said additional carboxylic group may be esterified with a ($C_{1-20}$)aliphatic alkyl group;

$R_1$ is an alkyl, alkylphenyl or aralkyl residue having from 1 to 30 carbon atoms;

$R_2$ is hydrogen, methyl or ethyl;

x is comprised between 0 and 50;

y is comprised between 0 and 30;

d) from 0 to about 20% by weight of at least one ethylenically unsaturated amide;

e) from about 0.2 to about 20% by weight of at least one diester between a polyoxyalkyleneglycol or an emulsifier having at least two free OH-groups and an ethylenically unsaturated carboxylic acid, as the cross-linking agent;

f) from 0 to about 20% by weight of at least one ethylenically unsaturated sulfonic acid.

Examples of ethylenically unsaturated mono- or dicarboxylic acids as indicated under a) are, for example, acrylic, methacrylic, itaconic, maleic, sorbic, crotonic acids, and analogs. Among these, acrylic and methacrylic acids are the preferred ones.

Preferred esters of ethylenically unsaturated mono- or dicarboxylic acids indicated under b) are methyl acrylate, ethyl acrylate, methyl methacrylate, butyl acrylate, ethyl methacrylate and analogs. The most preferred ones are methyl and ethyl (meth)acrylate.

The associative monomer c) may be any compound falling within the above formula $A-O-(CH_2-CHR_2O)_x-(CH_2)_y-R_1$ wherein $R_1$ and $R_2$ are as above indicated, the sum of x and y may vary between 0 and 80 and A is the acylic residue of an ethylenically unsaturated acid selected from acrylic, methacrylic, itaconic, maleic, sorbic, crotonic, oleic and linoleic acids. Preferred are the esters of cetylstearylalcohol ethoxylated with 25 moles of ethylene oxide. The associative monomers c) are commercially available products, or they can be prepared substantially according to procedures known in the art (U.S. Pat. Nos. 3,652,497 and 4,075,411).

The preferred ethylenically unsaturated amides d) are acrylamide, methacrylamide and vinylpyrrolidone, whereas the preferred ethylenically unsaturated sulfonic acids f) are vinylsulfonic acid and p-styrenesulfonic acid.

The cross-linking agents listed under point e) above can have one of the following structures of formula (I), (II) or (IV), or they are polyethoxylated derivatives of castor oil, optionally hydrogenated in whole or in part, esterified with ethylenically unsaturated carboxylic acids, with the proviso that the total number of ethylenic bonds is at least two.

In a first apect of the present invention, the cross-linking agent e) is a compound of formula (I):

$$D_1-O-(CH_2-CHZ_1-O-)_a-(CH_2-CHZ_2-O-)_b-(CH_2-CHZ_3-O)_c-D_2 \quad (I)$$

wherein:
$D_1$ and $D_2$, which can be the same or different, are an ethylenically unsaturated acylic residue, which may contain an additional carboxylic group wherein, optionally, said additional carboxylic group can be esterified with a $(C_{1-20})$aliphatic alkyl group;

$Z_1$ and $Z_3$ represent independently hydrogen or a $(C_{1-20})$ aliphatic alkyl or aralkyl group;

$Z_2$ is hydrogen or methyl;

a and c are integers comprised between 0 and 20;

b is an integer comprised between 1 and 100;

the sum a+b+c may represent any integer comprised between 1 and 140;

with the proviso that, when $Z_1$, $Z_2$ and $Z_3$ are simultaneously hydrogen and $D_1$ and $D_2$ are simultameously the acyl residue of methacrylic acid, the sum a+b+c cannot be 1;

and wherein the structure of the polyalkyleneglycol may be random or block.

Preferably, in the cross-linking agents of formula (I), $D_1$ and $D_2$ represent, independently, the acylic residue of acrylic, methacrylic, itaconic, maleic, sorbic, crotonic, oleic or linoleic acid, $Z_1$, $Z_2$ and $Z_3$ represent hydrogen or methyl, the sum a+b+c is higher than 10 and the structure of the polyalkyleneglycol may be random or block.

More preferably, in the cross-linking agents of formula (I), $D_1$ and $D_2$ represent, independently, the acylic residue of acrylic, methacrylic or itaconic acid, $Z_1$, $Z_2$ and $Z_3$ represent hydrogen, and the sum a+b+c is higher than 20.

The cross-linking agents of formula (I) are products deriving from the esterification of polyalkyleneglycols with ethylenically unsaturated carboxylic acids; some of them are described in the literature (U.S. Pat. Nos. 3,639,459, and 4,138,381; DD Patent 205,891; Polymer, 1978, 19(9), 1067–1073; Pigm. Resin. Technol., 1992, 21(5), 16–17).

The compounds of formula (I) can also be prepared by esterification of the compounds of formula (Ia)

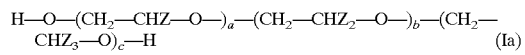

wherein $Z_1$, $Z_2$, $Z_3$, a, b and c are as above defined, with a carboxylic acid $D_1$—OH and/or $D_2$—OH, wherein $D_1$ and $D_2$ are as above defined, or the corresponding anhydride or acyl halide or, alternatively, by trans-esterification of the corresponding esters of low-boiling alcohols.

In a second aspect of the present invention, the cross-linking agent e) is a compound of formula (II)

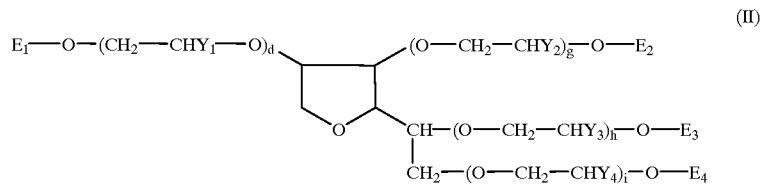

wherein:
$E_1$, $E_2$, $E_3$ and $E_4$ represent independently hydrogen or the acylic residue of a saturated or ethylenically unsaturated mono- or dicarboxylic acid from 2 to 25 carbon atoms, in which the further carboxylic group can optionally be esterified with a $(C_{1-20})$aliphatic alkyl group, with the proviso that at least two of $E_1$, $E_2$, $E_3$ and $E_4$ represent ethylenically unsaturated acylic residues as above defined;

$Y_1$, $Y_2$, $Y_3$ and $Y_4$, which can be the same or different, are hydrogen, methyl or ethyl;

d, g, h and i are integers comprised between 0 and 30.

Preferably, the compounds of formula (II) are sorbitan derivatives (all of d, g, h and i are 0) or sorbitan derivatives ethoxylated with from about 4 to about 20 moles of ethylene oxide, in which at least two of the hydroxy groups are esterified with ethylenically unsaturated carboxylic acids selected from acrylic, methacrylic, itaconic, maleic, sorbic, crotonic, oleic and linoleic acids, and at least one of the two residual hydroxy groups is esterified with a fatty acid from 10 to carbon atoms.

The compounds of formula (II) are prepared by introducing the ethylenically unsaturated acyl groups as reported above in the preparation of the compounds of formula (I). The starting substrate is a compound of formula (II) wherein at least two of $E_1$, $E_2$, $E_3$ and $E_4$ represent hydrogen, and the remaining of $E_1$, $E_2$, $E_3$ and $E_4$ can be hydrogen or an acyl group as above defined.

In a third aspect of the present invention, the cross-linking agent e) is a polyethxoxylated derivative of castor oil, optionally partially or totally hydrogenated, esterified with an ethylenically unsaturated carboxylic acid, with the proviso that, in said cross-linking agent, the total number of bonds of ethylenic type is at least two. Preferred are the polyethoxylated derivatives of castor oil with an ethoxylation degree varying from about 15 to about 150, esterified with acids selected from acrylic, methacrylic, itaconic, maleic, sorbic, crotonic, oleic and linoleic acids.

These compounds are prepared by esterification of the corresponding polyethxoxylated derivatives of castor oil, optionally partially or totally hydrogenated, following procedures known in the art.

In a fourth aspect of the present invention, the cross-linking agent e) is a compound of formula (IV)

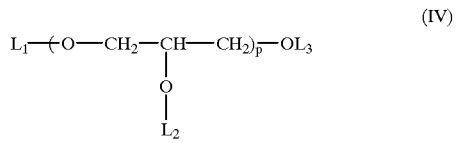

(IV)

wherein:
  $L_1$, $L_2$ and $L_3$, which may be the same or different, are hydrogen or an acyl residue of a saturated or unsaturated mono- or dicarboxylic acid from 2 to 25 carbon atoms, in which the further carboxylic group can optionally be esterified with a $(C_{1-20})$aliphatic alkyl group, with the proviso that at least two of $L_1$, $L_2$ and $L_3$ represent an ethylenically unsaturated acylic residue as above defined;
  p is an integer comprised between 2 and 50.

Also in this case, the preferred ethylenically unsaturated acyl residue derive from acids selected from acrylic, methacrylic, itaconic, maleic, sorbic, crotonic, oleic and linoleic acids.

Also the compounds of formula (IV) are prepared through the above illustrated conventional procedures, starting from a polyglycerol of formula (IVa):

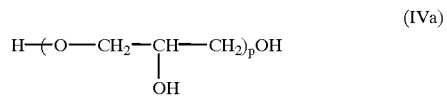

(IVa)

Some of these cross-linking agents are new; accordingly, they represent a further object of the present invention.

The above described cross-linking agents have been identified by means of $^1$H NMR and $^{13}$C NMR (spectrometer: BRUKER ARX 300). The analysis of the obtained spectra has confirmed that the percentage of the residual OH-groups after the esterification is negligible.

As illustrated above, the amounts in which the cross-linking agents are employed may vary within wide limits. Preferably, amounts of cross-linking agents are used higher than 0.3% of the total weight of the monomers. More preferably, the amounts of cross-linking agents are higher than 1.0% of the total weight of the monomers.

The cross-linked copolymers of the invention can be prepared by different polymerization procedures such as, for instance, the precipitation polymerization, suspension and solution polymerizations, or the emulsion polymerizations of the type oil-in-water or water-in-oil. The conditions of the polymerization reactions are, basically, those known in the art. Generally, the polymerizations are performed in the presence of anionic surfactants/emulsifiers, such as, for instance, sodium dodecylbenzenesulfonate, sodium disecondary-butylnaphthalene sulfonate, sodium laurylsulfate, sodium laurylether sulfate, disodium dodecyldiphenyl ether disulphonate, disodium n-octadecylsulfosuccinamate or sodium dioctylsulfosuccinate. Particularly preferred are sodium laurylsulfate and sodium laurylether sulfate. The temperature is generally comprised between about 50 and about 120° C., and the polymerization is completed in about 2–8 hours. The most preferred polymerization reaction is the oil-in-water emulsion polymerization.

The invention is further illustrated by the following examples.

EXAMPLES A–AC

Examples A–AC, reported in the following, describe the preparation of the cross-linking agents e).

The so obtained cross-linking agents will hereinafter be identified through the letter/s of the relevant preparation, as indicated in Table 1.

Though the esterification products described in the present invention can be obtained by means of different synthetic pathways such as, for instance, the transesterifications or the condensation with acyl halides, the following illustrative examples report direct esterifications with carboxylic acids using, as an example, xylene or n-octane as the solvents, in the presence of acids like 95% sulfuric acids, or esterifications performed with anhydrides, in the absence of solvents and acids.

The reactions were carried out in a glass reactor equipped with stirrer, thermometer, Dean-Stark apparatus or reflux condenser, depending on whether an acid or an anhydride is used, and diffuser through which air is blowed for the whole duration of the reaction, in order to keep active the polymerization inhibitor.

The reactor was charged with:
1) the precursors to be esterified, namely the compounds of formulae (Ia), (IIa), (IVa), or the polyethoxylated derivatives of castor oil;
2) the ethylenically unsaturated carboxylic acids, or the anhydrides in stoichiometric ratio with the hydroxy groups of the above precursors which one desires to esterify;
3) 0.5 by weight of sulfuric acid (not employed if the acylation reaction is carried out with anhydrides);
4) 1% by weight of hydroquinone monomethylether as the polymerization inhibitor;
said weight percentages being calculated on the total weight of the solids, and
5) an amount of solvent (xylene or n-octane, not employed if the acylation reaction is carried out with anhydrides) so as to have a weight per cent content of solids of 30.

The reaction mixture was refluxed until complete elimination of the water, in the presence of a steady air bubbling, in order to avoid the deactivation of the hydroquinone monomethylether (the polymerization inhibitor). Once the polymerization was terminated, the solvent was distilled off in vacuo, thus leaving a waxy product, pourable upon heating, which was employed as such in the subsequent polymerizations.

condensed moles of ethylene oxide per mole of starting castor oil; TWEEN® 80 (I.C.I.) is sorbitan monooleate ethoxylated with 20 moles of ethylene oxide; ELFACOS® (Akzo-Nobel) is a block copolymer of ethylene oxide with two blocks of polydodecylglycol; EMCOL® 14 is a polyglyceryl-4 oleate (Witco), monoester of oleic acid with tetraglycerol.

TABLE 1

Sinthesys of the cross-linking agents e)

| Preparation | Precursor | Unsaturated acid or anhydride | Solvent | Acid | Compound of formula/structure |
|---|---|---|---|---|---|
| Esterification of PEG 1000 | | | | | |
| A | PEG 1000 | Acrylic acid | n-octane | 95% $H_2SO_4$ | (I) |
| B | PEG 1000 | Maleic anhydride | — | — | (I) |
| C | PEG 1000 | Methacrylic anhydride | — | — | (I) |
| D | PEG 1000 | Methacrylic acid | n-octane | 95% $H_2SO_4$ | (I) |
| Esterification of PEGs with different average molecular weight | | | | | |
| E | PEG 1000 | Itaconic acid | n-octane | 95% $H_2SO_4$ | (I) |
| F | PEG 2000 | Itaconic acid | n-octane | 95% $H_2SO_4$ | (I) |
| G | PEG 3000 | Itaconic acid | n-octane | 95% $H_2SO_4$ | (I) |
| H | PEG 12000 | Itaconic acid | n-octane | 95% $H_2SO_4$ | (I) |
| Esterification of PPG and Copolymers PEG/PPG | | | | | |
| I | PLURONIC L122 | Itaconic acid | n-octane | 95% $H_2SO_4$ | (I) |
| J | PLURONIC F-68 | Itaconic acid | n-octane | 95% $H_2SO_4$ | (I) |
| K | PLURONIC 63N10 | Itaconic acid | n-octane | 95% $H_2SO_4$ | (I) |
| L | PPG 600 | Itaconic acid | n-octane | 95% $H_2SO_4$ | (I) |
| Esterification of copolymers PEG/dodecylglycols (ELFACOS ®) | | | | | |
| M | ELFACOS ST37 | Itaconic acid | n-octane | 95% $H_2SO_4$ | (I) |
| N | ELFACOS ST37 | Acrylic acid | n-octane | 95% $H_2SO_4$ | (I) |
| Esterification of castor oil 57EO | | | | | |
| O | C. oil 57EO | Sorbic acid | Xylene | 95% $H_2SO_4$ | C. oil 57EO di- and trisorbate |
| P | C. oil 57EO | Itaconic acid | n-octane | 95% $H_2SO_4$ | C. oil 57EO di- and triitaconate |
| Q | C. oil 57EO | Itaconic acid | n-octane | 95% $H_2SO_4$ | do |
| R | C. oil 57EO | Acrylic acid | n-octane | 95% $H_2SO_4$ | C. oil 57EO di- and triacrylate |
| S | C. oil 57EO | Maleic anhydride | — | — | C. oil 57EO di- and trimaleate |
| Esterification of TWEEN ® | | | | | |
| T | TWEEN 80 | Itaconic acid | n-octane | 95% $H_2SO_4$ | (II) |
| U | TWEEN 80 | Acrylic acid | n-octane | 95% $H_2SO_4$ | (II) |
| V | TWEEN 20 | Itaconic acid | n-octane | 95% $H_2SO_4$ | (II) |
| W | TWEEN 20 | Acrylic acid | n-octane | 95% $H_2SO_4$ | (II) |
| Esterification of castor oil with different ethoxylation degrees | | | | | |
| X | C. oil 30EO | Itaconic acid | n-octane | 95% $H_2SO_4$ | C. oil 30EO di- and triitaconate |
| Y | C oil 80EO | Itaconic acid | n-octane | 95% $H_2SO_4$ | C. oil 80EO di- and triitaconate |
| Esterification of EMCOL ® 14 | | | | | |
| Z | EMCOL 14 | Acrylic acid | n-octane | 95% $H_2SO_4$ | (IV) |
| AA | EMCOL 14 | Itaconic acid | n-octane | 95% $H_2SO_4$ | (IV) |
| AB | EMCOL 14 | Methacrylic acid | n-octane | 95% $H_2SO_4$ | (IV) |
| AC | EMCOL 14 | Maleic anhydride | — | — | (IV) |

Table 1 lists the so obtained cross-linking agents e). In this Table, PEG means polyethylene glycol and the number which follows represents its average molecular weight; PLURONIC® L122, F-68 and 63N10 are copolymers of polyethylene and polypropylene glycols; PPG stands for polypropylene glycol and the number which follows represents its average molecular weight; "c. oil" means castor oil, where the number followed by EO represents the number of

EXAMPLES 1–4

Comparative Examples

The following examples refer to preparations described in EP A1 0013836, 0109820 and 0658579; they were carried out to compare the art known copolymers with those of the present invention.

A 2 liter glass reactor, equipped with stirrer, reflux condenser, thermometer and thermostated bath, was charged with 336.6 ml of deionized water, then nitrogen was bubbled for 30 minutes. Under nitrogen stream, the reactor was subsequently charged with 6.6 g of an aqueous 28% by weight solution of sodium laurylsulfate and 18.725 ml of a monomeric emulsion composed of 127.6 g of deionized water, 126.8 g of ethyl acrylate, 92.7 g of methacrylic acid, 6.6 g of an aqueous 28% by weight solution of sodium laurylsulfate, 36 ml of a 0.7% by weight solution of ammonium persulfate and 24.3 g of the associative monomer c), which is cetylstearyl alcohol ethoxylated with 25 moles of ethylene oxide [identified in the following Table 2 as ($C_{16-18}$)alcohol 25OE] esterified with an acid selcted from acrylic, methacrylic, itaconic and sorbic acid, respectively. The temperature was brought to 85° C. and kept at this value for 20 minutes, then the remainder of the monomeric emulsion and 20 ml of a 0.7% by weight solution of ammonium persulfate were added over 180 minutes, while keeping the temperature at 85° C. The so obtained acrylic emulsion was cooled and discharged from the reactor.

To evaluate the thickening and suspending properties of the so obtained non cross-linked copolymers, a 1.5% solution of the selected copolymer was neutralized with an aqueous 10% by weight solution of sodium hydroxide. The thickening properties of the so obtained gels were determined with a Brookfield viscosimeter (spindle RV7, T: 20° C.); the suspending properties, expressed as "yield value", were determined by difference of the viscosities measured at 1 rpm and 0.5 rpm, divided by 100.

Table 2 reports the results obtained with the four preparations.

TABLE 2

| Preparation | Associative monomer c) | Viscosity 20 rpm*, Cps | Yield value |
|---|---|---|---|
| 1 | ($C_{16-18}$) alcohol 25OE acrylate | 50000 | 2950 |
| 2 | ($C_{16-18}$) alcohol 25OE methacrylate | 51000 | 2750 |
| 3 | ($C_{16-18}$) alcohol 25OE itaconate | 48000 | 2800 |
| 4 | ($C_{16-18}$) alcohol 25OE sorbate | 50000 | 2800 | rpm*: rounds per minute
Cps: centipoises

EXAMPLES 5–50

The cross-linked copolymers of the present invention were prepared by operating as described in Examples 1–4, in the presence of the cross-linking agent e) and, optionally, of the monomers d) and/or f).

A 2 liter glass reactor, equipped with stirrer, reflux condenser, thermometer and thermostated bath was charged with 336.6 ml of deionized water, then nitrogen was bubbled for 30 minutes. Under nitrogen stream, the reactor was subsequently charged with 6.6 g of an aqueous 28% by weight solution of sodium laurylsulfate and 18.725 ml of a monomeric emulsion composed of 127.6 g of deionized water, 219.5 g of the monomers previously described under points a), b), d) and f) in the reciprocal per cent composition described in the following Table, 6.6 g of an aqueous 28% by weight solution of sodium laurylsulfate, 36 ml of a 0.7% by weight solution of ammonium persulfate and 24.3 g of the associative monomer c), which is cetylstearyl alcohol ethoxylated with 25 moles of ethylene oxide [again identified in the following Table 3 as ($C_{16-18}$)alcohol 25OE] esterified with an acid selcted from acrylic, methacrylic, itaconic and sorbic acid, and an amount of cross-linking agent e) selected from those previously mentioned in Table 1 under Examples A–AC, as indicated in Table 3. The temperature was brought to 85° C. and kept at this value for 20 minutes, then the remainder of the monomeric emulsion and 20 ml of a 0.7% by weight solution of ammonium persulfate were added over 180 minutes, while keeping the temperature at 85° C. The so obtained acrylic emulsion was cooled and discharged from the reactor.

To evaluate the thickening and suspending properties of the so obtained cross-linked copolymers in aqueous systems, a 1.5% solution of the selected copolymer was neutralized with an aqueous 10% by weight solution of sodium hydroxide. The thickening and suspending properties, the latter again expressed as "yield value", of the cross-linked copolymers of the invention were determined as above illustrated in Examples 1–4.

The following Table 3 reports the obtained results.

In this Table, the term "cross-linking agent" means a component e) which is identified through the alphabet letter/s as in Table 1, the "component c)" is cetylstearyl alcohol esterified as indicated in Table 3, "monomer composition" represents the employed mixture of monomers referred to under points a), b), d) and f) above, where:

EA stands for ethyl acrylate [component b)];

MAA stands for methacrylic acid [component a)];

VP stands for vinylpyrrolidone [component d)];

MAAm stands for methacrylamide [component d)];

VSA stands for vinylsulfonic acid [component f)];

and the numbers which follow said acronyms indicate the reciprocal weight percentages of the employed monomers in the "monomer composition". As an example, EA/MAA 60/40 means that the monomer composition comprises 60% by weight of ethyl acrylate and 40% by weight of methacrylic acid.

In any case, the amounts of the single components which are employed fall within the above indicated percentages, namely those which refer to the composition of the monomeric system adopted for preparing the copolymer of the present invention.

TABLE 3

| Copolymer of Ex. | Crosslinking agent e) (grams) | Component c) | Monomer composition (components a, b, c, d, f) | Viscosity (cps, 20 rpm) | Yield value |
|---|---|---|---|---|---|
| 5 | P (15) | ($C_{16-18}$) alcohol 25OE sorbate | EA/MAA 60/40 | 52000 | 3300 |
| 6 | P (15) | ($C_{16-18}$) alcohol 25OE acrylate | EA/MAA 60/40 | 60000 | 5200 |
| 7 | R (15) | ($C_{16-18}$) alcohol 25OE acrylate | EA/MAA 60/40 | 66000 | 4400 |
| 8 | P (15) | ($C_{16-18}$) alcohol 25OE acrylate | EA/MAA/MAAm 55/40/5 | 53000 | 4000 |
| 9 | P (15) | ($C_{16-18}$) alcohol 25OE acrylate | EA/MAA/VP 55/40/5 | 65000 | 5400 |

TABLE 3-continued

| Copolymer of Ex. | Crosslinking agent e) (grams) | Component c) | Monomer composition (components a, b, c, d, f) | Viscosity (cps, 20 rpm) | Yield value |
|---|---|---|---|---|---|
| 10 | P (15) | ($C_{16-18}$) alcohol 25OE acrylate | EA/MAA/VSA 55/43/2 | 52000 | 4100 |
| 11 | L (3) | ($C_{16-18}$) alcohol 25OE itaconate | EA/MAA 60/40 | 70000 | 6400 |
| 12 | A (4, 5) | ($C_{16-18}$) alcohol 25OE itaconate | EA/MAA 60/40 | 64000 | 5600 |
| 13 | B (6) | ($C_{16-18}$) alcohol 25OE itaconate | EA/MAA 60/40 | 56000 | 4000 |
| 14 | A (4) | ($C_{16-18}$) alcohol 25OE methacrylate | EA/MAA 60/40 | 67000 | 4400 |
| 15 | C (5) | ($C_{16-18}$) alcohol 25OE methacrylate | EA/MAA 60/40 | 60000 | 5000 |
| 16 | A (4) | ($C_{16-18}$) alcohol 25OE methacrylate | EA/MAA/MAAm 55/40/5 | 62500 | 4500 |
| 17 | D (4) | ($C_{16-18}$) alcohol 25OE methacrylate | EA/MAA 60/40 | 60000 | 5000 |
| 18 | A (4) | ($C_{16-18}$) alcohol 25OE methacrylate | EA/MAA/VP 55/40/5 | 65000 | 5400 |
| 19 | A (4) | ($C_{16-18}$) alcohol 25OE methacrylate | EA/MAA/VSA 55/43/2 | 62000 | 4500 |
| 20 | G (8) | ($C_{16-18}$) alcohol 25OE acrylate | EA/MAA 60/40 | 58000 | 5000 |
| 21 | A (4) | ($C_{16-18}$) alcohol 25OE acrylate | EA/MAA 60/40 | 69000 | 6400 |
| 22 | A (3.3) | ($C_{16-18}$) alcohol 25OE acrylate | EA/MAA 50/50 | 60000 | 6000 |
| 23 | F (6) | ($C_{16-18}$) alcohol 25OE itaconate | EA/MAA 60/40 | 62000 | 6000 |
| 24 | E (3.4) | ($C_{16-18}$) alcohol 25OE itaconate | EA/MAA/VP 55/40/5 | 58000 | 5000 |
| 25 | E (4.0) | ($C_{16-18}$) alcohol 25OE acrylate | EA/MAA/VP 53/39/8 | 55000 | 4500 |
| 26 | T (10) | ($C_{16-18}$) alcohol 25OE acrylate | EA/MAA/MAAm 55/40/5 | 56000 | 5000 |
| 27 | F (4) | ($C_{16-18}$) alcohol 25OE itaconate | EA/MAA 60/40 | 60000 | 5800 |
| 28 | T (10) | ($C_{16-18}$) alcohol 25OE acrylate | EA/MAA/VP 55/40/5 | 54000 | 4800 |
| 29 | T (10) | ($C_{16-18}$) alcohol 25OE acrylate | EA/MAA/VSA 55/43/2 | 53000 | 4800 |
| 30 | T (10) | ($C_{16-18}$) alcohol 25OE acrylate | EA/MAA 60/40 | 52000 | 4000 |
| 31 | U (10) | ($C_{16-18}$) alcohol 25OE acrylate | EA/MAA 60/40 | 54000 | 4500 |
| 32 | V (10) | ($C_{16-18}$) alcohol 25OE acrylate | EA/MAA 60/40 | 53500 | 4200 |
| 33 | W (10) | ($C_{16-18}$) alcohol 25OE acrylate | EA/MAA 60/40 | 58000 | 4800 |
| 34 | I (6) | ($C_{16-18}$) alcohol 25OE acrylate | EA/MAA 60/40 | 53000 | 3500 |
| 35 | J (8) | ($C_{16-18}$) alcohol 25OE acrylate | EA/MAA 60/40 | 64000 | 4200 |
| 36 | F (5) | ($C_{16-18}$) alcohol 25OE itaconate | EA/MAA 60/40 | 60000 | 5700 |
| 37 | E (4) | ($C_{16-18}$) alcohol 25OE itaconate | EA/MAA 60/40 | 50000 | 5200 |
| 38 | E (4.5) | ($C_{16-18}$) alcohol 25OE itaconate | EA/MAA 60/40 | 60000 | 5600 |
| 39 | E (4.5) | ($C_{16-18}$) alcohol 25OE acrylate | EA/MAA 60/40 | 56000 | 5000 |
| 40 | K (8) | ($C_{16-18}$) alcohol 25OE acrylate | EA/MAA 60/40 | 62000 | 4100 |
| 41 | K (8) | ($C_{16-18}$) alcohol 25OE acrylate | EA/MAA/MAAm 55/40/5 | 64000 | 5800 |
| 42 | K (8) | ($C_{16-18}$) alcohol 25OE acrylate | EA/MAA/VP 55/40/5 | 65000 | 5800 |
| 43 | K (8) | ($C_{16-18}$) alcohol 25OE acrylate | EA/MAA/VSA 55/43/2 | 58000 | 4300 |
| 44 | M (10) | ($C_{16-18}$) alcohol 25OE acrylate | EA/MAA 60/40 | 52000 | 4500 |
| 45 | N (10) | ($C_{16-18}$) alcohol 25OE acrylate | EA/MAA 60/40 | 51500 | 4200 |
| 46 | Z (10) | ($C_{16-18}$) alcohol 25OE acrylate | EA/MAA 60/40 | 56000 | 4800 |
| 47 | AA (10) | ($C_{16-18}$) alcohol 25OE acrylate | EA/MAA 60/40 | 56000 | 6000 |
| 48 | AB (10) | ($C_{16-18}$) alcohol 25OE acrylate | EA/MAA 60/40 | 55000 | 4100 |
| 49 | AC (10) | ($C_{16-18}$) alcohol 25OE acrylate | EA/MAA 60/40 | 60000 | 4900 |
| 50 | Q (11.5) | ($C_{16-18}$) alcohol 25OE acrylate | EA/MAA 60/40 | 44000 | 3800 |

The cross-linked copolymers of the present invention are useful thickening agents of aqueous, or substantially aqueous systems in a variety of fields such as, for instance, the cosmetic and textile industry. In addition, owing to their excellent suspending properties in comparison with those of the corresponding non cross-linked products, aqueous based cosmetic compositions can be formulated in which the rheology remains substantially unchanged after a long period of time, or aqueous based print pastes can be prepared having a satisfactory color yield, even when small amounts of said compounds are employed. These thickened compositions represent a further object of the present invention.

The following examples report the preparation of cosmetic compositions and printing pastes thickened with representative cross-linked copolymers of the present invention.

EXAMPLE A

A thickened oil-in-water facial cream is prepared by (the indicated percentages are by weight):

| 1. Cetearyl polyglucose | 3.00% |
|---|---|
| 2. Glyceryl stearate | 1.00% |
| 3. Cetearyl alcohol | 1.00% |
| 4. Coco caprylate/caprate | 5.00% |
| 5. Isopropyl palmitate | 5.00% |
| 6. Dioctyl ether | 5.00% |
| 7. Shea butter | 2.00% |
| 8. Tocopheryl acetate | 1.00% |
| 9. Antioxydant | 0.05% |
| 10. Demineralized water | q.s. to 100% |
| 11. Laureth-4 phosphate | 0.50% |
| 12. Imidazolydinyl urea | 0.30% |
| 13. Methylparaben | 0.20% |
| 14. Propylparaben | 0.10% |
| 15. Butylene glycol | 2.00% |
| 16. Perfume | 0.20% |
| 17. Thickening agent | 1.00% |
| 18. Sodium hydroxide (10% sol.) | q.s. to pH 6.5 |

The blend of the components 1→9 is heated at 70° C. (phase A). Separately, the water is heated at 70° C. and added with the component 11 (phase B). Phase A is added to phase B and and the resulting mixture is homogenized. After cooling to 40° C., the mixture is added with the emulsion of the components 12→15 and with the perfume. After subsequent cooling to room temperature, the thickening agent 17 is added under slow stirring, and the mixture is finally neutralized with component 18.

Thickened oil-in-water facial creams were prepared by using as the thickening agents the cross-linked copolymers of Examples 10, 12, 14, 21, 22, 27, 36 and 38. It was found that the viscosity and the rheology of the so prepared facial creams remained substantially unchanged for several weeks. On the other hand, an identical cream thickened with the non cross-linked copolymer of Example 3 tended to increase its viscosity along the time, to become sticky and loose its homogeneity upon manipulation.

EXAMPLE B

A thickened eye contour gel is prepared by (the indicated percentages are by weight):

| 1. Demineralized water | q.s. to 100% |
|---|---|
| 2. Imidazolidinyl urea | 0.30% |
| 3. Methyl paraben | 0.20% |
| 4. Thickening agent | 3.00% |
| 5. Sodium hydroxide (10% sol.) | q.s to pH 7.0 |
| 6. PEG-400 | 1.00% |
| 7. Panthenol | 1.00% |
| 8. Saccharide Isomerate | 2.00% |
| 9. PEG-35 castor oil and guaiazulene | 0.10% |

The components 2 and 3 are dissolved in water at room temperature, then the thickening agent 4 is added under slow stirring and the resulting mixture is neutralized with 5. The so obtained gel is added with the mixture of components 6→9, and the whole is stirred to homogeneity.

Thickened eye contour gels were prepared by using as the thickening agents the cross-linked copolymers of Examples 10, 12, 14, 21, 22, 27, 36 and 38. It was found that the viscosity and the rheology of the so prepared gels remained substantially unchanged for several weeks. On the other hand, an identical eye contour gel thickened with the non cross-linked copolymer of Example 3 tended to increase its viscosity along the time, to become sticky and loose its homogeneity upon manipulation.

EXAMPLE C

A hair fixative gel is prepared by (the indicated percentages are by weight):

| 1) Demineralized water | q.s. to 100% |
|---|---|
| 2) Thickening aqent | 4.00% |
| 3) Imidazolidinyl urea | 0.30% |
| 4) Methylparaben | 0.20% |
| 5) Sodium hydroxide (10% sol.) | q.s. to pH 7.0 |
| 6) Ethyl alcohol 95% | 3.00 |
| 7) PVP | 2.00% |
| 8) Glycerin | 1.00% |
| 9) Panthenol | 1.00% |
| 10) PEG20 glyceryl ricinoleate and ricinoleamide DEA | 0.70% |
| 11) Perfume | 0.20% |

Components 3 and 4 are dissolved in water at room temperature, then the thickening agent is added under slow stirring and the whole is neutralized with component 5. Separately, component 7 is dissolved in component 6 and the resulting blend is added to the previously formed gel. The mixture is added with components 8 and 9 and, finally, with the blend of components 10 and 11.

Similar results as those obtained in Examples A and B were achieved also with this cosmetic peparation.

EXAMPLE D

Preparation of a Print Paste

An aqueous based print paste was prepared by (the indicated percentages are by weight):

| 1) Demineralized water | 81.00% |
|---|---|
| 2) Defoprint A (silicon defoamer) | 0.002% |
| 3) Ammonia (25% solution) | 0.006% |
| 4) Legoprint AN (acrylic binder) | 0.110% |
| 5) Fixol ST (color fixing agent) | 0.009% |
| 6) BLU HELIZARIN ® RT (color pigment) | 0.030% |
| 7) Thickening agent | 0.031% |

Components 1, 4 and 5 are commercial products sold by 3V SIGMA S.p.A., Bergamo, Italy.

Tests were carried out by flat and rotatory printing on different fibers (hydrophilic cotton, partially hydrophilic cotton, polyester/cotton:50/50 mixture), and using, as the thickening agents, the cross-linked copolymers of Examples 6, 8, 9, 24 and 50. In all cases, the achieved color yields were absolutely satisfactory.

I claim:

1. Cross-linked copolymers obtained by copolymerization of a monomeric system comprising:
   a) from about 10 to about 97% by weight of at least one ethylenically unsaturated mono- or dicarboxylic acid;
   b) from 0 to about 80% by weight of at least one $(C_{1-20})$alkyl or aralkyl ester of an ethylenically unsaturated mono- or dicarboxylic acid;
   c) from about 0.5 to about 80% by weight of at least one associative monomer which is an ester of formula

$$A\text{—}O\text{—}(CH_2CHR_2O)_x\text{—}(CH_2)_y\text{—}R_1$$

wherein
   A is an ethylenically unsaturated acylic residue, optionally containing an additional carboxylic group, wherein, optionally, said additional carboxylic group may be esterified with a $(C_{1-20})$aliphatic alkyl group;
   $R_1$ is an alkyl, alkylphenyl or aralkyl residue having from 1 to 30 carbon atoms;
   $R_2$ is hydrogen, methyl or ethyl;
   x is comprised between 0 and 50;
   y is comprised between 0 and 30;
   d) from 0 to about 20% by weight of at least one ethylenically unsaturated amide;
   e) from about 0.2 to about 20% by weight of at least one cross-linking agent selected from the group consisting of a diester of an ethylenically unsaturated carboxylic acid and a polyoxyalkyleneglycol containing more than 10 oxyalkylene units and a diester of an ethylenically unsaturated carboxylic acid and an emulsifier having at least two free OH-groups;
   f) from 0 to about 20% by weight of at least one ethylenically unsaturated sulfonic add.

2. Cross-linked copolymers as defined in claim 1, wherein the cross-linking agent e) is a compound of formula (I):

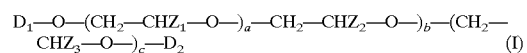

$$D_1\text{—}O\text{—}(CH_2\text{—}CHZ_1\text{—}O\text{—})_a\text{—}CH_2\text{—}CHZ_2\text{—}O\text{—})_b\text{—}(CH_2\text{—}CHZ_3\text{—}O\text{—})_c\text{—}D_2 \quad (I)$$

wherein:

$D_1$ and $D_2$, which can be the same or different, are an ethylenically unsaturated acylic residue, which may contain an additional carboxylic group wherein, optionally, said additional carboxylic group can be esterified with a ($C_{1-20}$)aliphatic alkyl group;

$Z_1$ and $Z_3$ represent independently hydrogen or a ($C_{1-20}$) aliphatic alkyl or aralkyl group;

$Z_2$ is hydrogen or methyl;

a and c are integers comprised between 0 and 20;

b is an integer comprised between 1 and 100;

the sum a+b+c may represent any integer comprised between 11 and 140;

and wherein the structure of the polyalkyleneglycol may be random or block.

3. Cross-linked copolymers as defined in claim 2, wherein $D_1$ and $D_2$ represent, independently, the acylic residue of acrylic, methacrylic, itaconic, maleic, sorbic, crotonic, oleic or linoleic acid, $Z_1$, $Z_2$ and $Z_3$ represent hydrogen or methyl, and the structure of the polyalkyleneglycol may be random or block.

4. Cross-linked copolymers as defined in claim 2, wherein $D_1$ and $D_2$ represent, independently, the acylic residue of acrylic, methacrylic or itaconic acid, $Z_1$, $Z_2$ and $Z_3$ represent hydrogen, and the sum a+b+c is higher than 20.

5. Cross-linked copolymers as defined in claim 1, wherein the cross-linking agent e) derived from an emulsifier having at least two free —OH groups is a compound of formula (II):

8. Cross-linked copolymers as defined in claim 7, wherein the polyethoxylated derivative of castor oil has an ethoxylation degree varying from about 15 to about 150 and is esterified with at least one acid selected from the group consisting of acrylic, methacrylic, itaconic, maleic, sorbic, crotonic, oleic, and linoleic acids.

9. Cross-linked copolymers as defined in claim 1, wherein the cross-linking agent e) derived from an emulsifier having at least two free —OH groups is a compound of formula (IV)

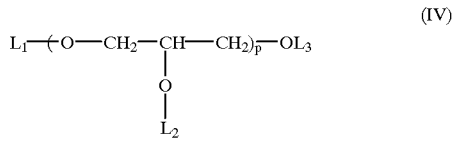

wherein:

$L_1$, $L_2$ and $L_3$, which may be the same or different, are hydrogen or an acyl residue of a saturated or unsaturated mono- or dicarboxylic acid from 2 to 25 carbon atoms, in which the further carboxylic group can optionally be esterified with a ($C_{1-20}$)aliphatic alkyl group, with the proviso that at least two of $L_1$, $L_2$ and $L_3$ represent an ethylenically unsaturated acylic residue as above defined;

p is an integer comprised between 2 and 50.

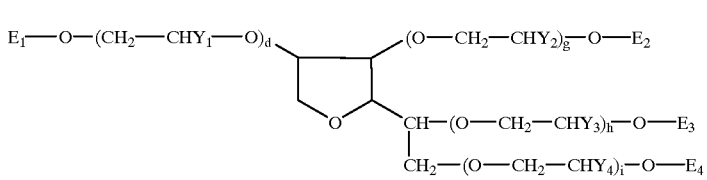

wherein:

$E_1$, $E_2$, $E_3$ and $E_4$ represent independently hydrogen or the acylic residue of a saturated or ethylenically unsaturated mono- or dicarboxylic acid from 2 to 25 carbon atoms, in which the further carboxylic group can optionally be esterified with a ($C_{1-20}$)aliphatic alkyl group, with the proviso that at least two of $E_1$, $E_2$, $E_3$ and $E_4$ represent ethylenically unsaturated acylic residues as above defined;

$Y_1$, $Y_2$, $Y_3$ and $Y_4$, which can be the same or different, are hydrogen, methyl or ethyl;

d, g, h and i are integers comprised between 0 and 30.

6. Cross-linked copolymers as defined in claim 5, wherein the compounds of formula (II) are sorbitan derivatives or sorbitan derivatives ethoxylated with from about 4 to about 20 moles of ethylene oxide, in which at least two of the hydroxy groups are esterified with ethylenically unsaturated carboxylic acids selected from the group consisting of acrylic, methacrylic, itaconic, maleic, sorbic, crotonic, oleic and linoleic acids, and at least one of the two residual hydroxy groups is esterified with a fatty acid from 10 to 25 carbon atoms.

7. Cross-linked copolymers as defined in claim 1, wherein the cross-linking agent e), derived from an emulsifier having at least two free —OH groups, is a polyethoxylated derivative of castor oil, optionally partially or totally hydrogenated, esterified with an ethylenically unsaturated carboxylic acid, with the proviso that, in said cross-linking agent, the total number of ethylenic bonds is at least two.

10. Cross-linked copolymers as defined in claim 9, wherein $L_1$, $L_2$ and $L_3$, which may be the same or different, represent independently the ethylenically unsaturated acyl residues of acrylic, methacrylic, itaconic, maleic, sorbic, crotonic, oleic, or linoleic acids.

11. Cross-linked copolymers as defined in claim 1, wherein the component a) of the monomeric mixture is an ethylenically unsaturated carboxylic acid selected from the group consisting of acrylic, methacrylic, itaconic, maleic, sorbic and crotonic acids.

12. Cross-linked copolymers as defined in claim 1, wherein the component b) of the monomeric mixture is an ester selected from the group consisting of methyl acrylate, ethyl acrylate, methyl methacrylate, butyl acrylate and ethyl methacrylate.

13. Cross-linked copolymers as defined in claim 12, wherein the component b) of the monomeric mixture is an ester selected from the group consisting of methyl acrylate, ethyl acrylate, methyl methacrylate and ethyl methacrylate.

14. Cross-linked copolymers as defined in claim 1, wherein, in the associative monomer c), $R_1$ and $R_2$ are as above indicated, the sum of x and y may vary between 0 and 80 and A is the acylic residue of an ethylenically unsaturated acid selected from the group consisting of acrylic, methacrylic, itaconic, maleic, sorbic, crotonic, oleic and linoleic acids.

15. Cross-linked copolymers as defined in claim 14, wherein the associative monomer c) is an ester of an ethylenically unsaturated acid, selected from the group consisting of acrylic, methacrylic, itaconic, maleic, sorbic, crotonic, oleic, and linoleic acids, esterified with a mixture of cetyl and stearyl alcohols ethoxylated with 25 moles of ethylene oxide.

16. Cross-linked copolymers as defined in claim 1, wherein the component d) of the monomeric mixture is an ethylenically unsaturated amide selected from the group consisting of acrylamide, methacrylamide and vinylpyrrolidone.

17. Cross-linked copolymers as defined in claim 1, wherein the component f) of the monomeric mixture is selected from the group consisting of vinylsulfonic acid and p-styrene sulfonic acid.

18. Cross-linked copolymers as defined in claim 1, in which the cross-linking agent e) is used in amounts higher than 0.3% of the total weight of the monomers of the monomeric system.

19. Cross-linked copolymers as defined in claim 18, in which the cross-linking agent e) is used in amounts higher than 1% of the total weight of the monomers of the monomeric system.

20. Cross-linked copolymers as defined in claim 1, prepared by an emulsion polymerization process.

* * * * *